US005445631A

United States Patent [19]

Uchida

[11] Patent Number: 5,445,631

[45] Date of Patent: Aug. 29, 1995

[54] FLUID DELIVERY SYSTEM

[75] Inventor: Tadatoshi Uchida, Tokorozawa, Japan

[73] Assignees: Suntory Limited; Nissho Corporation, both of Osaka, Japan

[21] Appl. No.: 192,282

[22] Filed: Feb. 4, 1994

[30] Foreign Application Priority Data

Feb. 5, 1993 [JP] Japan ........................ 5-042041

[51] Int. Cl.[6] .................. A61B 19/00; A61M 5/32

[52] U.S. Cl. .................. 604/412; 604/88; 604/413

[58] Field of Search .................. 604/82, 87, 88, 201, 604/202, 403, 411, 412, 413, 416; 141/329

[56] References Cited

U.S. PATENT DOCUMENTS

| | | | |
|---|---|---|---|
| 3,872,867 | 3/1975 | Killinger | 141/329 |
| 3,987,791 | 10/1976 | Chittenden et al. | 604/413 |
| 3,995,630 | 12/1976 | van de Veerdonk | 604/202 |
| 4,583,971 | 4/1986 | Bocquet et al. . | |
| 4,614,437 | 9/1986 | Buehler | 604/88 X |
| 4,614,515 | 9/1986 | Tripp et al. . | |
| 4,615,267 | 9/1986 | Larkin . | |
| 4,675,020 | 6/1987 | McPhee | 604/411 |
| 4,757,911 | 7/1988 | Larkin et al. . | |
| 4,936,445 | 6/1990 | Grabenkort . | |
| 4,936,841 | 6/1990 | Aoki et al. | 604/82 |
| 5,033,476 | 7/1991 | Kasai | 604/413 |
| 5,171,214 | 12/1992 | Kolber et al. | 604/82 |
| 5,342,346 | 8/1994 | Honda et al. | 604/412 |
| 5,354,287 | 10/1994 | Wacks | 604/403 |

FOREIGN PATENT DOCUMENTS

| | | |
|---|---|---|
| 0565103 | 10/1993 | European Pat. Off. . |
| 2293916 | 7/1976 | France . |
| 3817101 | 10/1989 | Germany . |
| 59-209535 | 11/1984 | Japan . |
| 62-137056 | 6/1987 | Japan . |
| 63-135642 | 9/1988 | Japan . |
| 2-1277 | 1/1990 | Japan . |
| 2-4375 | 1/1990 | Japan . |
| 2-26506 | 6/1990 | Japan . |
| 3-37067 | 10/1991 | Japan . |
| 4-22745 | 5/1992 | Japan . |
| 4-282160 | 10/1992 | Japan . |
| 4-126545 | 11/1992 | Japan . |
| 4-329956 | 11/1992 | Japan . |
| WO93/21891 | 11/1993 | WIPO . |

*Primary Examiner*—C. Fred Rosenbaum
*Assistant Examiner*—Frank Wilkens, III
*Attorney, Agent, or Firm*—Burns, Doane, Swecker & Mathis

[57] ABSTRACT

A fluid delivery system including a vial having an opening for containing a dry medicament, a container having an opening for containing a solution, upper and lower, pierceable plugs for hermetically sealing the openings of the vial and the container, respectively, a capsule having upper and lower ends, and a sliding member slidably disposed in the capsule and having a double-pointed cannula providing with upper and lower needles. The container is slidably inserted into the capsule from the upper open end of the capsule and the vial can be detachably and fixedly connected to the lower open end of the capsule. When container is pushed downward, the lower needle of the cannula is firstly pierced and inserted into the plug of the vial so that the cannula is communicated with the medicament vial and then the upper needle of the cannula is pierced and inserted into the plug of the container so that the vial and the container are communicated to each other through the cannula.

18 Claims, 4 Drawing Sheets

FLUID DELIVERY SYSTEM

BACKGROUND OF THE INVENTION

1. Field of the Invention

This invention relates to a fluid delivery system, and more particularly, to such a fluid delivery system including a vial for containing therein a substance, preferably a powder, such as medicament or drug, and a container for containing therein a fluid, preferably a liquid, such as solution or diluent, to mix the powder with the liquid to obtain a medical solution.

2. Description of the Related Art

In hospitals or other health case facilities, dry medicament, such as powdered medicament or freeze-dried medicament, packaged within a container, such as a vial, has been conventionally used in such a manner that the above-mentioned medicament is mixed with or dissolved in a solution, which is to be provided for fluid therapy. In this case, the vial containing the medicament and another container containing a solution or diluent are connected to each other by means of a double-pointed hollow needle or any other communicating pipe, so that the solution is transferred to the vial containing the medicament to dissolve the latter.

However, such an operation requires laborious and troublesome works and, moreover, there is a fear of contamination because a hole for connection is formed on the container for drug in the open air.

To solve such problems, a fluid delivery system having an object of carrying out an operation in a completely sterile condition has been proposed, such as disclosed in Japanese Unexamined Patent Publications (kohyo) No. 61-501129 (which corresponds to U.S. Pat. No. 4,583,971), (kokai) No. 2-1277 (which corresponds to U.S. Pat. No. 4,936,841), and (kokai) No. 3-37067. A fluid storage and delivery system which cannot expect a complete sterile operation, but capable of optionally selecting the combinations between the medicament and solution and attaining a substantially sterile operation, has been proposed, such as disclosed in Japanese Unexamined Patent Publications (kokai) Nos. 59-209535, 62-137056, and 2-4375, or also Japanese Examined Patent Publications (kokoku) No. 2-26506.

In the above-mentioned JP-A 61-501129, a capsule accommodating a medicament container and a flexible container containing a solution are connected to each other by a tube, in such a manner that the medicament container is mutually communicated with the flexible container by communicating means provided in the tube and therefore the medicament is mixed with the solution in a sterile condition. Also, in JP-A 2-1277, capsule accommodating a medicament container is connected by its connecting portion to an opening of a solution container. The connecting portion of the capsule is accompanied with a communicating means providing with a means for controlling the connection order, in such a manner that the medicament container is first pierced by the communicating means and then the solution container is pierced so that the two containers are mutually communicated by the communicating means and therefore the medicament is mixed with the solution in a sterile condition. In JP-A 3-37067, a medicament container, a communicating means and a solution container are arranged in such an order and covered air tightly with a sheet made of synthetic resin. A container support means is provided between the medicament container and the solution container for supporting them over the sheet, so that the medicament container and the solution container are prevented from accessing toward each other until they are mutually communicated in a sterile condition.

On the other hand, JP-A 59-209535 discloses a system comprising a first hermetically sealed flexible container having a flexible wall member, a second container having a detachable stopper and which can be fixed through the wall member, and a stopper detaching means having a portion engaged with the stopper. The stopper comes into engaged with the stopper detaching means through the first and second containers and then the stopper is removed from the second container together with a sealing barrier of the first flexible container, so that the two containers are mutually communicated to allow the mixing of the contents in these containers. JP-A 62-137056 and JP-A 2-4375 discloses a system in which the above-mentioned second container is improved. Also, JP-A 2-26506 discloses a further improved system of that disclosed in the above-mentioned JP-A 59-209535.

Also, Unexamined Patent Publication (kokai) No. 4-329956 discloses a sterile mixing apparatus of medicament container in a sealed vial, the apparatus comprising a vial containing therein a medicament, a liquid container, pierceable plug members for hermetically sealing the openings of the vial and the container, respectively, a cannula member having respective edges at both sides. When the vial is pushed down to said container, one of needle tips of the cannula is first pierced and inserted into the medicament vial and then the other needle tip of the cannula is pierced to the fluid container, so that the medicament vial and the fluid container are communicated to each other through the cannula.

However, in the former system as disclosed in JP-A 61-501129, since a pair of the medicament container and the solution container are constructed as one unit, an operation in a complete sterile condition can be attained, although the kind of medicament which can be used in this system is restricted. On the other hand, the system disclosed in JP-A 59-209535 is relatively complicate in construction and has some drawbacks. For example, the stopper is undesirably dropped in the first container. It is difficult to obtain an operation in a complete sterile operation, although a substantially sterile operation can be attained. Also, since combination between the medicament container and the solution container can optionally be selected, suitable managing and handling would strongly be required in the medical field.

In the system discloses JP-A 4-329956, a special mechanism or means is necessary for retaining the medicament vial so as not to communicate with liquid container until the vial is intentionally pushed down to toward the container by an operator.

SUMMARY OF THE INVENTION

An object of the present invention is to provide a fluid delivery system which can be easily and surely handled by an operator, such as a doctor, nurse or the like, in a sterile or substantially sterile condition and has a simple construction as compared with the above-mentioned systems known in the prior art.

Accordingly to the present invention, there is provided with a fluid delivery system comprising: a vial having an opening for containing therein a substance which can be dissolved by a liquid; a container having an opening for containing therein the fluid; pierceable plug members for hermetically sealing said openings of the vial and the container, respectively; a cylindrical capsule having first and second open ends; a sliding member slidably disposed in said capsule and providing with a double-pointed cannula having upper and lower needles; said vial being detachably and fixedly connected to said first open end of the capsule; said container being slidably inserted into said capsule from said second open end thereof; and said lower and upper needles being sealingly pierced and inserted into said plugs of the vial and the container, respectively, so that said vial and said container are communicated to each other through said cannula, when said container is pushed toward said vial.

It is preferable that said container has a cylindrical wall portion and a bottom, an auxiliary cover member is put upon said container to air tightly cover said cylindrical wall portion and said bottom thereof, and said cover member is frictionally and slidably fit within said capsule, when said container is inserted into said capsule.

In another aspect of the present invention, there is provided a fluid delivery system comprising: a vial having an opening for containing therein a substance which can be dissolved by a liquid; a container having an opening for containing therein the fluid; first and second, pierceable plug members for hermetically sealing said openings of the vial and the container, respectively; a capsule having first and second open ends; a sliding member slidably disposed in said capsule and having a double-pointed cannula having lower and upper needles axially extending toward said first and second open ends, respectively; said vial being detachably and fixedly connected to said first open end of the capsule; said container being slidably inserted into said capsule from said second open end thereof; and means for controlling a movement of said sliding member in such a manner that, when said container is pushed toward said vial, said lower needle of the cannula is first sealingly pierced and inserted into said first plug of the vial so that said cannula is communicated with said vial and then said upper needle of the cannula is sealingly pierced and inserted into said second plug of the fluid container so that said vial and said fluid container are communicated to each other through said cannula.

DESCRIPTION OF THE PREFERRED EMBODIMENTS

Figure 1:
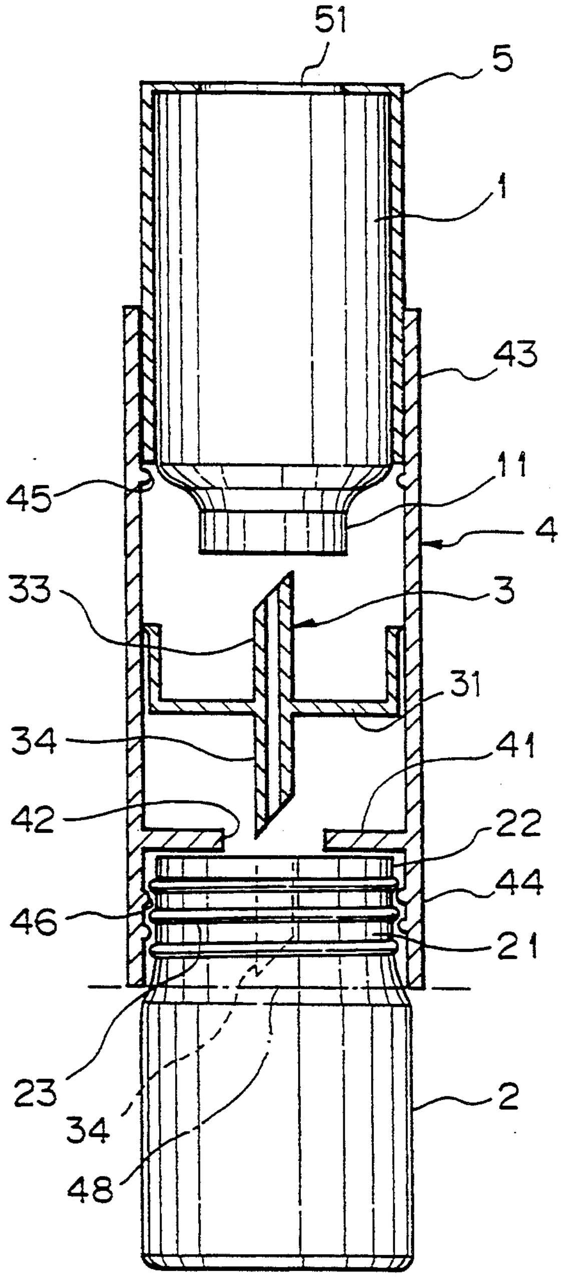
FIG. 1 is a cross-sectional view of a first embodiment of a fluid delivery system according to the present invention.
Figure 2:
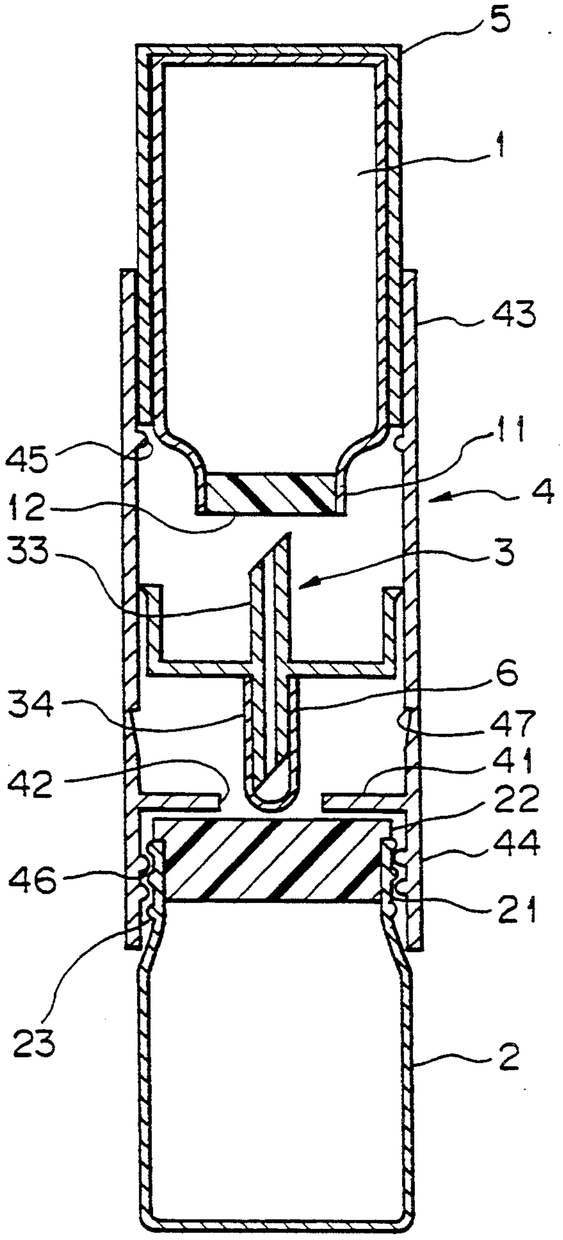
FIG. 2 is a cross-sectional view of another embodiment of the system similar to that of FIG. 1.
Figure 3:
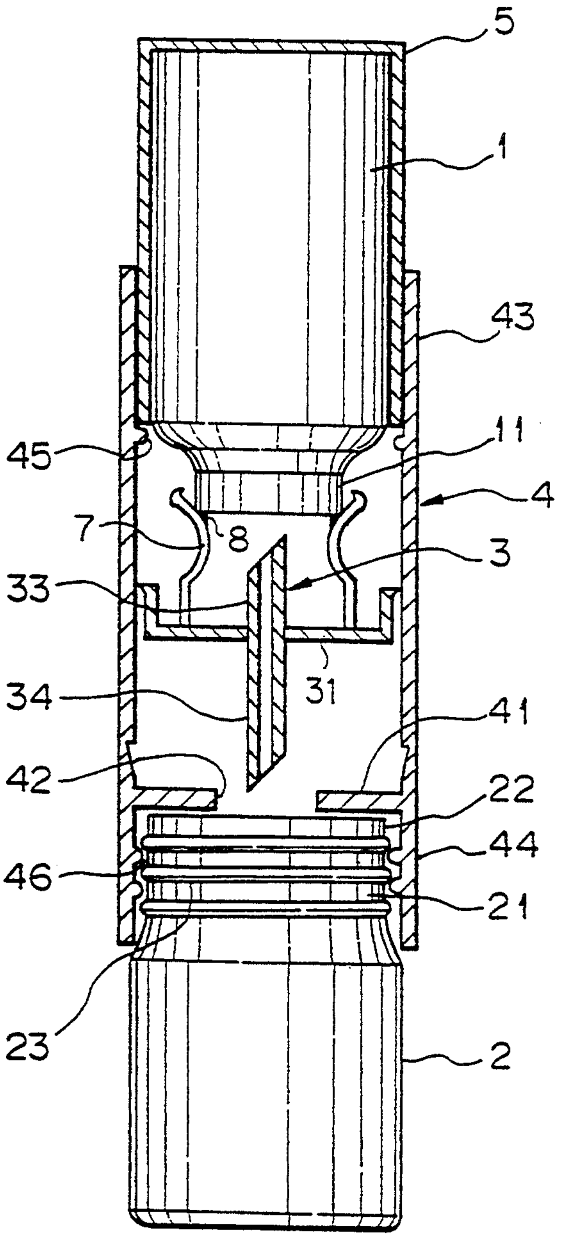
FIG. 3 is a cross-sectional view of a still another embodiment of the system.

Referring now to the drawings, wherein FIGS. 1, 2, and 3 show several embodiments of a fluid delivery system according to the present invention. The system comprises a fluid container 1, a vial 2, a sliding member 3 having a double-pointed cannula and a cylindrical or pipe-like capsule 4.

The capsule 4 has a partition wall 41 having a central opening 42 to separate this capsule 4 into two sections 43 and 44, i.e., an upper, slide section 43 having an inner cylindrical bore, within which the sliding member 3 is slidably disposed, and has an upper open end through which the solution container 1 is slidably inserted, and a lower, vial mount section 44 having a bottom open end to which the vial 2 is detachably and fixedly connected. The capsule 4 may be made of any suitable synthetic resin, such as polyetylene, polypropylene, polyestere or the like.

The solution container 1 is substantially cylindrical and usually made of glass or synthetic resin, such as polyetylene, polypropylene, polyestere or the like. The container 1 has an inlet opening 11 through which any suitable liquid, such as solution or diluent for transfusion, is filled and then the opening 11 is hermetically sealed by a pierceable, rubber plug 12.

The container 1 has a cylindrical wall portion and a bottom and it is preferable that the container 1 is sheathed within an auxiliary sliding cover 5 to air tightly cover the cylindrical wall portion and the bottom of the container 1. The cover 5 is not always necessary to cover entirely the bottom of the container 1, but may be provided with a central open area 51 as illustrated in FIG. 1, although at least the peripheral area of the bottom must be tightly covered by the auxiliary cover 5.

Such an auxiliary sliding cover 5 may be made of any suitable material, such as synthetic resin, for example polypropylene, polyetylene, polyvinyl chloride or the like, so that the auxiliary sliding cover 5 is frictionally, air tightly and slidably fit within the capsule 4 when the container 1 is inserted into the capsule 4. In addition, the capsule 4 is provided with an annular rib 45 on the inner wall thereof. Therefore, an annular edge of the cover 5 first comes into engage with the annular rib 45 to retain the container 1 within the capsule 4 when the solution container 1 is inserted into the capsule 4. Thus, the solution container 4 is prevented from unintentionally falling down. As described hereinafter in detail, when the container is further pushed down, the cover 5 is allowed to move over the annular rib 45.

The vial 2 is substantially cylindrical and usually made of glass and an inlet opening 21 through which the vial 2 is filled with any suitable substance, such as a dry medicament or drug, for example powdered medicament or freeze-dried medicament, not shown in the drawings. The inlet opening 21 is hermetically sealed by a pierceable, rubber plug 22. The vial 2 is provided with a male thread portion 23 around the inlet opening 21 and, on the other hand, the vial mount section 44 of the capsule 4 provided with a female thread portion 46, so that the vial 1 can be detachably and fixedly connected to the vial mount section 44 of the capsule 4 by the thread connection. The male and female thread portions 23 and 46 are arranged in such a manner that, when the vial 1 is fixedly connected to the capsule 4 by the thread connection, the upper surface of the rubber plug 22 of the vial 2 comes into contact with the radial partition wall 41.

Figure 4:
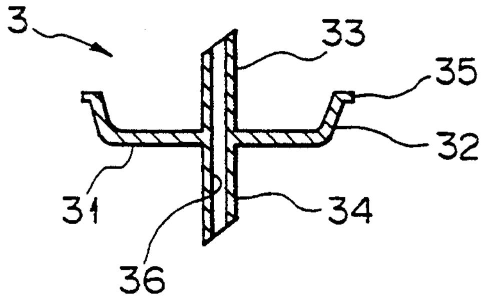
FIG. 4 is a cross-sectional view of a sliding member having a double-pointed cannula used in this system.
Figure 5:
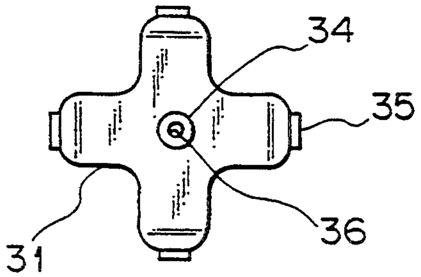
FIG. 5 is a bottom plan view of the sliding member shown in FIG. 4.
Figure 6:
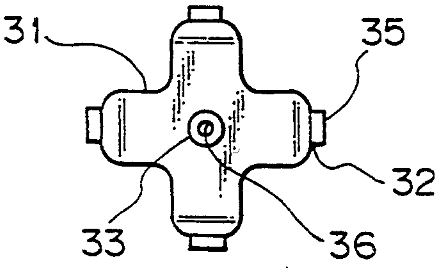
FIG. 6 is a top plan view of the sliding member.

The sliding member 3 is disposed in the slide section 43 of the capsule 4 so that the sliding member 3 is slidably moved in the axial direction within the cylindrical bore of the capsule 4. As also shown in FIGS. 4–6, the sliding member 3 comprises a cannula providing with upper and lower needles 33 and 34 extending axially toward the upper container 1 and lower vial 2, respectively, a hub 31 and several (four, in the embodiment shown in FIGS. 4–6) slide arms 32 extending axially from the periphery of the hub 31. The hub 31 and the slide arms 32 are integrally formed of any suitable synthetic resin as a single unit. The cannula is usually made of stainless steel, preferably SUS 304, or any hard synthetic resin, providing with upper and lower needles 33 and 34 extending axially up and down toward the container 1 and vial 2, respectively. The hub 31 is usually made of any suitable synthetic resin.

If a sharpness or pierceable property of the cannula is to be an important factor, the cannula should be made of stainless steel. On the other hand, if a disposable property of the cannula is to be an important factor, the cannula should be made of hard synthetic resin, such as ABS resin or polycarbonate. In this case, the sliding member 3 including the cannula, the hub 31 and the slide arms 35 can be integrally formed as a single unit.

When assembling this system, the sliding member 3 is first inserted into the slide section 43 of the capsule 4 so that the slide arms 35 are slidably engaged with the inner bore wall of the capsule 4 to retain the sliding member 3 within the capsule 4. Then, container 1 covered with the auxiliary cover 5 as mentioned above is inserted into the capsule 4 until the annular edge of the cover 5 comes into engage with the annular rib 45. Thus, the container 1 is retained within the capsule 4 so that the solution container 1 is prevented from unintentionally falling down. In this state, if necessary, the container 1 can also be sold and available in the market as a single product or good.

Usually, in the hospitals or other health case facilities, the vial 2 containing the medicament therein is connected to the capsule 4, as mentioned above and shown in FIGS. 1–3, by an operator, such as a doctor or nurse, so that the vial 2 and the capsule 4 are fixed to each other by the thread engagement. Then, the container 1 is pushed down so that the cover 5 moves over the annular rib 45. After the rubber plug 12 of the container 1 comes into contact with the upper needle 33 of the cannula, the sliding member 3 is further moved downward with the container 1 and then the lower needle 34 of the cannula comes into contact with rubber plug 22 of the vial 2 through the central opening 42 of the partition wall 41.

Then, according to the present invention, a movement of the sliding member 3 is controlled in such a manner that the lower needle 34 of the cannula is first sealingly pierced and inserted into the rubber plug 22 of the vial 2 so that the cannula is communicated with the vial 2 and then the upper needle 33 of the cannula is sealingly pierced and inserted into the rubber plug 12 of the fluid container 1 so that both the fluid container 1 and the vial 2 are communicated to each other through the cannula.

In order to ensure such an operation, it is preferable to form the cannula in such a manner that the edge of lower needle 34 is made sharper than that of the upper needle 33. In another embodiment, the rubber plug 12 of the container 1 is made harder than the rubber plug 22 of the vial 2.

In the embodiment shown in FIG. 2, a rubber cap 6 is attached to cover the lower needle 34 of the cannula which would prevent a leak of solution from the container 1 through the cannula, if the upper needle 33 was inserted into the rubber plug 12 of the container 1 to communicate with the container 1, before the lower needle 34 was pierced into the rubber plug 22 of the vial 2.

However, in the embodiment shown in FIG. 3, the sliding member 3 is provided with braking means to prevent a leak of solution from the container 1. Such braking means is comprised several legs 7 integrally extending from the hub 31 of the sliding member 3 and engaged with the opening portion of the container 1 by curved portions of projections 8 of the legs 7. Therefore, when the container 1 is pushed down, the sliding member 3 is lowered with the container 1 until the lower needle 34 of the cannula comes into contact with rubber plug 22 of the vial 2 and pierced into the rubber plug 22 of the vial 2 so that the cannula is communicated with the vial 1. After the hub 31 of the sliding member 3 comes into contact with the partition wall 41, the container 1 is moved over the projections 8 of the legs 7 and allowed to move downward so as to widen the legs 7, until the upper needle 33 was inserted into the rubber plug 12 of the container 1 to communicate with the container 1.

Also, as shown in the embodiments shown in FIGS. 2 and 3, a stopper means, such as an annular recess or undercut portion 47 is formed on an inner wall of the capsule 4. Therefore, when the sliding member 3 is completely lowered to a predetermined position, in other words, when the sliding member 3 comes into contact with the radial partition wall 42, the slide arms 32 of sliding member 3 comes to be engaged with the recess 47 and thus the sliding member 3 is locked. To more firmly lock the sliding member 3, the recess 47 is preferably formed as a sharp edge and on the other hand, the ends of the slide arms 32 are provided with hook portions 35, as shown in FIGS. 4–6, which can be surely engaged with the recess 47. Thus, after the sliding member 3 is once locked, its unfavorable movement, such as a raise or kick back thereof due to an elastic force of the rubber cap 6 can effectively prevented.

Thus, the liquid or solution in the container 1 enters into the vial 2 and the powdered medicament or freeze-dried medicament is mixed with or dissolved in the solution. After the solution in the container 1 is completely transferred to the vial 2, the vial 2 is removed from the capsule 4. Then, the vial 1 containing the medicament solution is used in the transfusion for a patient. The remaining system including the container 1, the sliding member 3 and the capsule 4 are usually disposed. In this case, it is preferable that the lower needle 34 does not protrude from the lower end 48 of the sleeve, as shown in FIG. 1, and thus a safe handling of the system can be ensured, after the vial 1 is removed.

Figure 7:
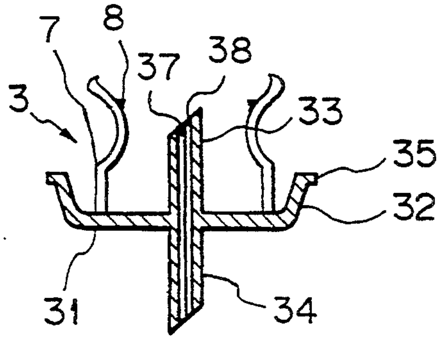
FIG. 7 is a cross-sectional view of a sliding member having another cannula.

Although in the above-mentioned embodiment, the cannula of the sliding member 3 has a single fluid passage 36, as shown in FIGS. 4–6, a cannula having two such passages 37 and 38 may be used, as shown in FIG. 7. In this case, the solution can be more rapidly transferred from the container 1 to the vial, since one of the passages 37 and 38 is used as a liquid way and the other is used as an air/gas way.

As mentioned above, according to the above-mentioned embodiment, since both the capsule 4 and the auxiliary cover 5 are made of synthetic resin, the auxiliary cover 5 is frictionally and air tightly fit within the capsule 4, even if the mutual dimensions therebetween have not been very strictly controlled. Therefore, any possible contamination is effectively prevented and, particularly, unfavorable substance, such as bacterium, is prevented from entering into the slide section 43 of the capsule 4.

Also, since the movement of the sliding member 3 is controlled in such a manner that the lower needle 34 of the cannula is firstly pierced and communicated with the vial 2 and then the upper needle 33 of the cannula is pierced into the rubber plug 12 of the fluid container 1 so that both the fluid container 1 and the vial 2 are communicated to each other through the cannula. Therefore, a safe operation can be attained in a sterile condition with the system having a relatively simple and less expensive construction.

Therefore, the fluid delivery system according to the present invention can easily be handled even if the operator is not familiar with the solution for transfusion and dry medicament in this field. Also, any possible errors in the delivery of mixing process for providing the patient can effectively be prevented.

It should be understood by those skilled in the art that the foregoing description relates to only a preferred embodiment of the disclosed invention, and that various changes and modifications may be made to the invention without departing from the spirit and scope thereof.

I claim:

1. A fluid delivery system comprising:

a vial having an opening for containing therein a substance which can be dissolved by a liquid;

a container having an opening for containing therein the liquid;

pierceable plug members for hermetically sealing the openings of the vial and the container, respectively;

a cylindrical capsule having first and second open ends;

a sliding member slidably disposed in the capsule and provided with a double-pointed cannula having upper and lower needles;

the vial being detachably and fixedly connected to the first open end of the capsule;

the container being slidably inserted into the capsule from the second open end thereof;

the upper and lower needles of the cannula piercing and being inserted into the plugs of the container and the vial, respectively, so that the vial and the container are communicated to each other through the cannula, when the container is pushed toward the vial;

the container having a cylindrical wall portion and a bottom; and an auxiliary cover member tightly covering the cylindrical wall portion and the bottom of the container, the cover member being frictionally, slidably and air tightly fit within the capsule when the cover member is inserted into the capsule.

2. A system as set forth in claim 1, wherein the capsule is provided with a partition wall to separate the capsule into two sections, i.e., a vial mount section having the first open end and a slide section having the second open end and within which the sliding member is slidably disposed, and the partition wall has a central hole through which the lower needle of the cannula of the sliding member is allowed to pass and inserted into the plug member of the vial.

3. A system as set forth in claim 2, wherein the vial is provided with a male thread around the opening and the slide section of the capsule is provided with a female thread at an inner wall thereof, so that the vial is detachably and fixedly connected to the first open end of the capsule by a thread connection.

4. A fluid delivery system comprising:

a vial having an opening for containing therein a substance which can be dissolved by a liquid;

a container having an opening for containing therein the liquid;

pierceable plug members for hermetically sealing the openings of the vial and the container, respectively;

a cylindrical capsule having first and second open ends;

a sliding member slidably disposed in the capsule and provided with a double-pointed cannula having upper and lower needles;

the vial being detachably and fixedly connected to the first open end of the capsule;

the container being slidably inserted into the capsule from the second open end thereof;

the upper and lower needles of the cannula piercing and being inserted into the plugs of the container and the vial, respectively, so that the vial and the container are communicated to each other through the cannula, when the container is pushed toward the vial, wherein the container has a cylindrical wall portion and a bottom, an auxiliary cover member is put onto the container to tightly cover the cylindrical wall portion and the bottom thereof, and the cover member is frictionally, slidably and air tightly fit within the capsule, when the container is inserted into the capsule, and wherein the capsule has an inner cylindrical wall provided with an annular rib, so that, when the container is inserted into the capsule, an annular edge of the cover member firstly comes into engagement with the annular rib to retain the container within the capsule and, when the container is further pushed in the capsules toward the vial, the cover member is allowed to come over the annular rib.

5. A fluid delivery system comprising:

a vial having an opening for containing therein a substance which can be dissolved by a liquid;

a container having an opening for containing therein a fluid;

first and second, pierceable plug members for hermetically sealing and closing the openings of the vial and the container, respectively;

a capsule having first and second open ends;

a sliding member slidably disposed in the capsule and having a double-pointed cannula provided with upper and lower needles axially extending toward the first and second open ends, respectively;

the vial being detachably and fixedly connected to the first open end of the capsule;

the container being slidably inserted into the capsule from the second open end thereof; and means for controlling a movement of the sliding member in such a manner that, when the container is pushed toward the vial, the lower needle of the cannula firstly pierces and is inserted into the first plug of the vial so that the cannula is communicated with the vial and then the upper needle of the cannula pierces and is inserted into the second plug of the fluid container so that the vial and the container are communicated to each other through the cannula.

6. A system as set forth in claim 5, wherein the container contains a liquid, such as solution or diluent for transfusion, and the vial contains a powder, such as medicament or drug.

7. A system as set forth in claim 5, wherein the control means comprises a braking means attached to the sliding member, the braking means is engagable with the container in such a manner that, when the container is pushed toward the vial, the sliding member is moved toward the vial with the container so that the lower needle of the cannula is pierced into the first plug of the vial and then the container moves over the braking means so that the upper needle of the cannula is pierced into the second plug of the fluid container.

8. A system as set forth in claim 5, wherein a rubber cap for covering the lower needle of the cannula is provided so as to prevent a leak of fluid from the container through the cannula, even if the upper needle is inserted into the second plug of the fluid container before the lower needle is pierced into the first plug of the vial.

9. A system as set forth in claim 5, wherein a stopper means for locking the sliding member with respect to the capsule is provided, when the sliding member is moved toward the vial to a predetermined position in which the lower needle of the cannula is completely inserted into the first plug of the vial.

10. A system as set forth in claim 9, wherein the stopper means comprises an annular recess formed on an inner wall of the capsule, so that the sliding member comes into fit in the recess and to be locked therein, when the sliding member is moved to the predetermined position.

11. A system as set forth in claim 5, wherein the capsule is provided with a partition wall to separate this capsule into two sections, i.e., a vial mount section having the first open end and a slide section having the second open end and within which the sliding member is slidably disposed, the partition wall has a central hole through which the lower needle of the cannula of the sliding member is allowed to pass and inserted into the plug member of the vial, so that the sliding member comes into contact with the partition wall, when the sliding member is moved toward the vial to a predetermined position in which the lower needle of the cannula is completely inserted into the first plug of the vial.

12. A system as set forth in claim 11, wherein the capsule has an inner cylindrical wail provided with an annular recess, so that the sliding member comes into fit in the recess and to be locked therein, when the sliding member is moved to the predetermined position.

13. A system as set forth in claim 12, wherein the vial is provided with a male thread around the opening and the vial mount section of the capsule is provided with a female thread at an inner wall thereof, so that the vial is detachably and fixedly connected to the first open end of the capsule by a thread connection.

14. A system as set forth in claim 13, wherein the male and female thread portions are arranged in such a manner that, when the vial is fixedly connected to the first open end of the capsule by a thread connection, a the first plug member of the vial comes into contact with the partition wall.

15. A system as set forth in claim 5, wherein the container has a cylindrical wall portion and a bottom, an auxiliary cover member tightly covering the cylindrical wall portion and the bottom thereof, and the cover member is frictionally, slidably and air tightly fit within the capsule, when the container is inserted into the capsule.

16. A fluid delivery system comprising:

a vial having an opening for containing therein a substance which can be dissolved by a liquid;

a container having an opening for containing therein a fluid;

first and second, pierceable plug members for hermetically sealing and closing the openings of the vial and the container, respectively;

a capsule having first and second open ends;

a sliding member slidably disposed in the capsule and having a double-pointed cannula provided with upper and lower needles axially extending toward the first and second open ends, respectively;

the vial being detachably and fixedly connected to the first open end of the capsule;

the container being slidably inserted into the capsule from the second open end thereof; and means for controlling a movement of the sliding member in such a manner that, when the container is pushed toward the vial, the lower needle of the cannula firstly pierce and is inserted into the first plug of the vial so that the cannula is communicated with the vial and then the upper needle of the cannula pierces and is inserted into the second plug of the fluid container so that the vial and the container are communicated to each other through the cannula, wherein the control means comprises the upper and lower needles of the cannula, in which an edge of the lower needles is sharper than an edge of the upper needle.

17. A fluid delivery system comprising:

a vial having an opening for containing therein a substance which can be dissolved by a liquid;

a container having an opening for containing therein a fluid;

first and second, pierceable plug members for hermetically sealing and closing the openings of the vial and the container, respectively;

a capsule having first and second open ends;

a sliding member slidably disposed in the capsule and having a double-pointed cannula provided with upper and lower needles axially extending toward the first and second open ends, respectively;

the vial being detachably and fixedly connected to the first open end of the capsule;

the container being slidably inserted into the capsule from the second open end thereof; and means for controlling a movement of the sliding member in such a manner that, when the container is pushed toward the vial, the lower needle of the cannula firstly pierces and is inserted into the first plug of the vial so that the cannula is communicated with the vial and then the upper needle of the cannula pierces and is inserted into the second plug of the fluid container so that the vial and the container are communicated to each other through the cannula, wherein the control means comprises the first and second, pierceable plug members made of rubber, in which a hardness of the second plug member is smaller than that of the first plug member.

18. A fluid delivery system comprising:

a vial having an opening for containing therein a substance which can be dissolved by a liquid;

a container having an opening for containing therein a fluid;

first and second, pierceable plug members for hermetically sealing and closing the openings of the vial and the container, respectively;

a capsule having first and second open ends;

a sliding member slidably disposed in the capsule and having a double-pointed cannula provided with upper and lower needles axially extending toward the first and second open ends, respectively;

the vial being detachably and fixedly connected to the first open end of the capsule;

the container being slidably inserted into the capsule from the second open end thereof; and means for controlling a movement of the sliding member in such a manner that, when the container is pushed toward the vial, the lower needle of the cannula firstly pierces and is inserted into the first plug of the vial so that the cannula is communicated with the vial and then the upper needle of the cannula pierces and is inserted into the second plug of the fluid container so that the vial and the container are communicated to each other through the cannula, wherein the container has a cylindrical wall portion and a bottom, an auxiliary cover member put onto the container to tightly cover the cylindrical wall portion and at least a part of the bottom thereof, and the cover member is frictionally, slidably and air tightly fit within the capsule, when the container is inserted into the capsule, and the capsule has an inner wall provided with an annular rib, so that, when the container is inserted into the capsule, an annular edge of the cover member firstly comes into engagement with the annular rib to retain the container within the capsule and, when the container is further inserted into the capsules, the cover member is allowed to move over the annular rib.

* * * * *